United States Patent [19]

Nguyen et al.

[11] Patent Number: 4,894,393
[45] Date of Patent: Jan. 16, 1990

[54] DITHIOCARBAMATE-CHOLINE ADDUTS AND USE THEREOF IN TREATMENT OF BRAIN DISEASES

[75] Inventors: Dat-Xuong Nguyen, Antony; Jean Rapin, Paris; Thadée Staron, Noisy le Roi, all of France

[73] Assignee: Lafon Pharma S.A., Fribourg, Switzerland

[21] Appl. No.: 245,243

[22] Filed: Sep. 16, 1988

[30] Foreign Application Priority Data

Sep. 18, 1987 [FR] France .................. 87 12968

[51] Int. Cl.⁴ .................. C07C 155/06; A61K 31/27
[52] U.S. Cl. .................. 514/476; 558/235
[58] Field of Search .................. 558/235; 514/476

[56] References Cited

U.S. PATENT DOCUMENTS 3,632,812  1/1972  Maier .................. 558/235

FOREIGN PATENT DOCUMENTS 0179694  4/1986  European Pat. Off. .......... 558/235
2445679  3/1975  Fed. Rep. of Germany ...... 558/235
488678   5/1970  Switzerland .................. 558/235

Primary Examiner—Alan L. Rotman
Assistant Examiner—Robert C. Whittenbaugh
Attorney, Agent, or Firm—Wegner & Bretschneider

[57] ABSTRACT

The subject of the invention is the choline diethyl-dithiocarbamate having the following structural formula:

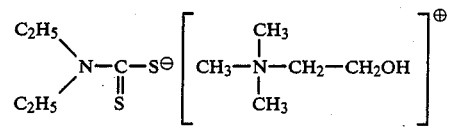

as well as a process for its preparation from choline chloride and sodium diethyl-dithio-carbamate trihydrate.

This substance is useful in the treatment of degenerative brain diseases.

7 Claims, No Drawings

DITHIOCARBAMATE-CHOLINE ADDUTS AND USE THEREOF IN TREATMENT OF BRAIN DISEASES

The subject of the present invention is a novel derivative of diethyl-dithio-carbamic acid, the choline diethyl-dithio-carbamate a process for its preparation and its therapeutic use.

The novel compound according to the invention, choline diethyl-dithio-carbamate, with the empirical formula $C_{10}H_{24}N_2OS_2$, corresponds to the following structural formula:

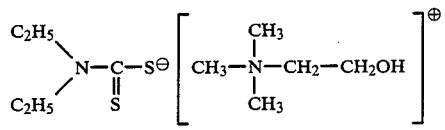

and has a molecular weight of 252.40.

This new salt of choline exists in the form of fine colourless or slighty yellowish crystals which have a melting point of 96°–97° C. and are readily soluble in water, alcohols and glycols, and are much less soluble in organic solvents.

The crystals of choline diethyl-dithio-carbamate are very hygroscopic and must be stored in a cold and hermetically sealed container.

The elemental analysis of the product gives the following results:

|  | calculated | found | mean |
|---|---|---|---|
| Carbon | 48.85% | 48.18–48.47 | 48.33% |
| Hydrogen | 9.64% | 9.37–9.54 | 9.45% |
| Nitrogen | 11.12% | 11.59–11.51 | 11.55% |
| Sulfur | 25.55% | 24.94–24.75 | 24.5% |
| Oxygen | 6.35% |  |  |

The I.R., U.V., N.M.R. and mass spectra clearly show the characteristic bands of the molecule of the novel product of the invention.

The choline diethyl-dithio-carbamate can be prepared by synthesis from sodium diethyl-dithio-carbamate trihydrate and choline chloride.

The reaction is the following:

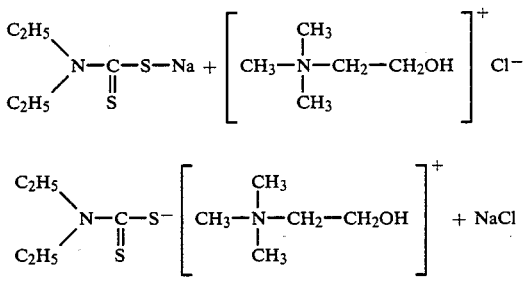

The synthesis can be carried out according to the following procedure:

In two Erlenmeyer flasks or 2 beakers of appropriate size are separately dissolved:

56 g (0.40 mole) of choline chloride in 100 ml of absolute ethanol by warming by means of a hot plate or water bath and by stirring the mixture to promote dissolution.

90 g (0.40 mole) of sodium diethyl-dithio-carbamate trihydrate in 100 ml of absolute ethanol.

When the two solutions are clear, the alcoholic solution of choline is poured slowly and gently into that of the sodium salt with vigorous stirring and external cooling by means of a bath of cold water because the reaction is very exothermic.

When about a third has been added, a copious precipitate is formed. The addition is continued while very vigorous stirring is maintained.

The addition of the alcoholic solution of choline to that of the sodium salt lasts about 15 minutes. Stirring is continued for a further 30 minutes. The mixture is then allowed to cool overnight. The receptacle contaning the reaction mixture is kept closed.

The following day the sodium chloride is removed by filtration and the filter is washed twice with 50 ml of absolute ethanol.

About 23 g of sodium chloride are recovered.

The alcoholic mother liquors (containing the diethyl-dithio-carbamate of choline dissolved in the ethanol) are concentrated under a water pump vacuum on a water bath to remove the excess of ethanol.

The very viscous residue is then poured rapidly into a beaker or mortar made of glass or porcelain. It is dried under a high vacuum in a desiccator containing phosphorus pentoxide as drying agent.

The product obtained is obtained in the form of a block which is reduced to fine crystals or a fine microcrystalline powder which is colourless or very slightly yellowish.

The yield of choline diethyl-dithio-carbamate is about 100 g.

The choline diethyl-dithio-carbamate thus obtained must be stored in a hermetically sealed container on account of its hygroscopic nature.

According to the present invention, the therapeutic properties of the novel choline salt have been demonstrated and a very comprehensive study has been made of its toxicity.

The toxicological study was conducted on the SWISS white mouse.

It was possible to study the acute toxicity, the chronic toxicity, the influence on fecundity, teratogenesis, fertility as a function of time and longevity, and the effect on the immune response of choline diethyl-dithio-carbamate in this animal.

For all of these experiments the animals were randomized, separated according to sex and distributed in groups of 30, the pregnant females being isolated in individual cages. These animals were fed on a suitable complete feed which they could consume ad libitum in order to avoid any deficiencies during the period of experimentation. They drank tap water, supplemented or not with the product to be tested, namely choline diethyl-dithio-carbamate.

The complete feed used contained cereals, plant proteins, animal proteins, mineral salts and vitamins.

The measurement of the acute toxicity of the new compound according to the invention administered by the intraperitoneal or subcutaneous route shows that the acute toxicity is very low:

Below 1 g/kg there were no deaths.

The LD 50 lies between 1.4 and 1.7 g/kg.

In order to estimate the chronic toxicity of the new compound according to the invention, a dose of 20 mg/kg per day of the new compound was administered orally in drinking water to 4 groups of 30 mice for 100 days. No harmful effect on the health of the animals was observed.

The effect of the new compound according to the invention on the fecundity and teratogenesis in SWISS white mice was examined. The experiments were continued over four generations of animals and showed that the groups receiving the new compound according to the invention, taken as a whole, had 15% more descendants than the controls, with the number of still-born mice less than half that of the controls.

The results are presented in the table below:

EXPERIMENTS ON FECUNDITY AND TERATOGENESIS CONDUCTED ON FOUR GENERATIONS OF 4 MONTHS OLD FEMALE SWISS WHITE MICE
(Groups C - controls; groups G - choline diethyl-dithio-carbamate at 1% in the drinking water)

| Generations | Number of mice verified to be pregnant at each generation | | Number of mice born live | | Number of mice still-born | | Number of resorbed foetuses | |
|---|---|---|---|---|---|---|---|---|
| | C | G | C | G | C | G | C | G |
| I | 30 | 30 | 255 | 249 | 7 | — | 15 | 2 |
| II | 30 | 30 | 242 | 316 | 5 | 2 | 9 | 2 |
| III | 30 | 30 | 258 | 324 | 8 | — | 8 | — |
| IV | 30 | 30 | 263 | 308 | 3 | — | 11 | — |
| Total | 120 | 120 | 1018 | 1197 | 23 | 2 | 43 | 4 |

Similarly, the determination of the fertility of the females as a function of their age showed that the administration of the new compound according to the invention substantially prolonged the period of fertility of the female mice as is shown in the table below:

EXPERIMENTS ON FERTILITY OF FEMALE SWISS MICE AS A FUNCTION OF THEIR AGE
(Groups C - controls; groups G - choline diethyl-dithio-carbamate at 1% in the drinking water).

| | % of fertile female mice | | average number of young mice per fertile female mouse | |
|---|---|---|---|---|
| | C | G | C | G |
| 4-months old mice | 97 | 97 | 8,5 | 9,8 |
| 8-months old mice | 62 | 92 | 6,9 | 8,0 |
| 15-months old mice | 23 | 60 | 5,2 | 7,5 |

Finally, with respect to the growth and longevity of the animals, it was observed that the new compound according to the invention did not have a negative influence on growth inspite of a reduction of about 25% in the intake of water and of about 5% in the intake of food. It was observed, on the contrary, that the administration of the new compound according to the invention considerably delayed ageing. This last activity is particular spectacular in the male mice and seems to be due to a modification of traits and behaviour leading to a diminution of the vulnerability which usually results from very high aggressiveness. The control male mice fought much more, exhausted themselves, wounded and killed each other.

EXPERIMENTS ON LONGEVITY

The effect of the new compound according to the invention has also been studied on the efficacy of the immune response in SWISS white mice.

The protection of the above animals against aggression is ensured by the immune system in association with the antigens of the major histocompatibility complex. The efficacy of the immune reaction depends on the mechanisms and associated equilibria which determine the principal parameters of competence (sensitivity, precision, intensity, duration). Thus, the multiple and various forms of aggression are usually brought under control rapidly without being consciously perceived by the host who is subjected to the aggression. When, however, inappropriate and erroneous responses are frequent, they become the source of many inflammatory diseases which are difficult to control and which usually become more marked with age. In these latter cases, a hygienic strategy and therapy are required to correct the errors of the immune system, control inflammation and re-establish the functioning of the tissues and the damaged areas.

The table below illustrates the potentiation of immune competence by the choline diethyl-dithio-carbamate. The table in fact shows that in order to obtain the same degree of immune protection, 100 mcg of a specific vaccine are required in the case of the control and mice and only 20 mcg are needed in the case of the mice treated with the compound according to the invention.

INFLUENCE OF THE CHOLINE DIETHYL-DITHIO-CARBAMATE ON THE EFFICACY OF THE IMMUNE RESPONSE IN THE MOUSE ON SUBCUTANEOUS INJECTION OF A PATHOGENIC *ESCHERICHIA COLI*
(C = control groups; G = groups supplied for 21 days with drinking water containing 1% of the choline diethyl-dithio-carbamate)

| | | Amounts of vaccine injected subcutaneously (mcg/25 g mouse) 8 days before the test pathogen | | | | | | | | | | | | | | |
|---|---|---|---|---|---|---|---|---|---|---|---|---|---|---|---|---|
| | | 0 | | 3 | | 10 | | 20 | | 50 | | 70 | | 100 | | 150 |
| | | C | G | C | G | C | G | C | G | C | G | C | G | C | G | C | G |
| Lethal dose (LD) in % of the pathogenic inoculum as a function of the dose of vaccine injected | $LD_0$ | | | | | | | | | + | | + | | + | + | + | + |
| | $LD_{30}$ | | | | + | | | | | | | | | | | | |
| | $LD_{50}$ | | | | | | | | | | | | + | | | | |
| | $LD_{70}$ | | | | | | + | | | + | | + | | | | | |
| | $LD_{100}$ | + | + | + | | + | | | | | | | | | | | |

All of the experiments related above lead to the conclusion that the toxicity of the new compound according to the invention is practically nil. It is also apparent that the administration of this new salt of choline to SWISS white mice brings about very favourable effects on fecundity, longevity, behaviour and the efficacy of the immune response.

The pharmacological studies of the new compound according to the invention have shown that it possesses a chelating effect on heavy and transition metals, an immuno-stimulant effect, an anti-degenerative effect and an effect on neuronal transfer, and that, in consequence, it exhibits a very valuable therapeutic activity in the area of degenerative brain diseases such as senile dementias, Alzheimer's disease and dementias of the Alzheimer type.

It is known that in these diseases the central cholinergic neurones are the first to be affected by the degeneration, whether at the level of the synthesis of the neurotransmitter: acetyl choline, or at the level of the membrane which requires choline for its biosynthesis. Now, from the therapeutic point of view, acetyl choline cannot be administered directly since it does not cross membranes and the results obtained by the administration of choline alone in the form of its chloride are quite inadequate.

The new compound according to the invention has been the subject of a number of experiments conducted in two animal models of nerve degeneration, caused either by destruction of basal cholinergic nuclei or by the repeated administration of aluminium hydroxide. It has been observed in both cases that the learning capacities of the animals, impaired as a result of degeneration, were found to be restored by oral administration of choline diethyl-dithio-carbamate according to the invention. After treatment for three weeks, a dose-related effect was observed and the measurements of the effective dose showed that the ED 50 lies between 0.10 g and 0.30 g/kg of body weight of the animal.

The clinical study of the choline diethyl-dithio-carbamate was conducted by performing clinical experiments on patients suffering from a degenerative brain disease, fully defined according to the DSM III criteria of the MMS, a thorough psychometric check-up and a SCANER X-ray.

The experiment was conducted double blind, at a hospital center with the following treatments for a period of six to twelve weeks:
placebo
choline chloride
choline diethyl-dithio-carbamate.

The doses of active substance used were 125 mg when taken orally three times a day, i.e. a daily dose of 375 mg.

The results show that in 70% of the cases treated by the compound according to the invention a suppession or significant reduction in the disorders of behaviour and mood of the patients is observed, these results being rendered objective by psychometric tests.

In the case of patients treated with placebo or choline chloride improvements were seen in only 30% of the cases and they were slight, not very clear-cut and less durable than those produced in patients treated with the new compound of the invention.

Another subject of the present invention is therapeutic compositions containing the diethyl-dithio-carbamate of choline as active principle. These compositions can be administered by the oral or rectal route or they can be injected depending on the physiopathological state of the digestive tract of the patients concerned.

In the case of oral administration, the pharmaceutical compositions of the invention are available in the form of capsules or tablets in which the active substance is combined with a suitable excipient, advantageously including silica gel in view of the highly hygroscopic nature of the choline diethyl-dithio-carbamate. Furthermore, in order to avoid premature hydrolysis of the latter in the stomach, it is necessary that the galenic envelope of these preparations be enteric in nature (microencapsulation, for example) for oral administration.

In the case of rectal administration, suppositories of standard composition can be prepared starting from the compound according to the invention.

In the case of injections, it is necessary to make provision for the separate packaging of the choline diethyl-dithio-carbamate and the physiological solution which needs to be added to it at the time of administration.

The dosage used for the novel pharmaceutical composition according to the invention varies between the daily administration of 250 mg and 2.5 g of active compound, it being understood that for oral administration the capsules or tablets preferably contain 125 mg of active substance and may be administered at a rate of 2 to 20 capsules or tablets per day, and that for rectal administration the suppositories contain 250 or 500 mg of active substance in a 3 g suppository.

The pharmaceutical compositions described above are given as illustrative and non-limiting examples of the present invention.

We claim:

1. Choline diethyl-dithio-carbamate having the formula:

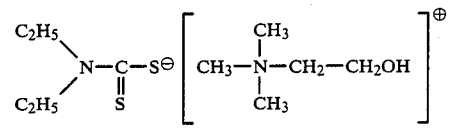

2. A therapeutic composition for the treatment of degenerative brain diseases of the class consisting of senile dementia, Alzheimer's Disease and dementias of the Alzheimer type, comprising an effective amount of choline diethyl-dithio-carbamate in a mixture with a pharmaceutically acceptable excipient.

3. A therapeutic composition as claimed in claim 2, in the form of capsules or tablets.

4. A therapeutic composition as claimed in claim 2, in the form of suppositories.

5. A therapeutic composition as claimed in claim 3, comprising capsules or tablets coated with an enteric substance.

6. A therapeutic composition as claimed in claim 2, comprising capsules or tablets containing an excipient which comprises silica gel.

7. Process for the treatment of degenerative brain diseases of the class consisting of senile dementia, Alzheimer's Disease and dementias of the Alzheimer type, which comprises administering to a human in need thereof an effective amount of choline diethyl-dithio-carbamate.

* * * * *